(12) United States Patent
Gastaldo et al.

(10) Patent No.: US 9,816,942 B2
(45) Date of Patent: Nov. 14, 2017

(54) DEVICE AND METHOD FOR INSPECTING SEMICONDUCTOR MATERIALS

(71) Applicant: Altatech Semiconductor, Montbonnot-Saint-Martin (FR)

(72) Inventors: Philippe Gastaldo, Pontcharra (FR); Viviane Leguy, Domene (FR)

(73) Assignee: ALTATECH SEMICONDUCTOR, Montbonnot-Saint-Martin (FR)

( * ) Notice: Subject to any disclaimer, the term of this patent is extended or adjusted under 35 U.S.C. 154(b) by 838 days.

(21) Appl. No.: 14/350,135

(22) PCT Filed: Oct. 4, 2012

(86) PCT No.: PCT/FR2012/000395
§ 371 (c)(1),
(2) Date: Apr. 7, 2014

(87) PCT Pub. No.: WO2013/050673
PCT Pub. Date: Apr. 11, 2013

(65) Prior Publication Data
US 2014/0285797 A1    Sep. 25, 2014

(30) Foreign Application Priority Data
Oct. 7, 2011    (FR) ...................... 11 03073

(51) Int. Cl.
*G06F 15/00*        (2006.01)
*G01N 21/95*        (2006.01)
(Continued)

(52) U.S. Cl.
CPC ......... *G01N 21/9501* (2013.01); *H01L 22/12* (2013.01)

(58) Field of Classification Search
CPC ................................................ G01N 21/9501
See application file for complete search history.

(56) References Cited

U.S. PATENT DOCUMENTS

2004/0184653 A1    9/2004    Baer et al.

FOREIGN PATENT DOCUMENTS

| FR | 2914422 A1 | 10/2008 |
| WO | 0023794 A1 | 4/2000 |
| WO | WO 00/23794 | * 4/2000 |

OTHER PUBLICATIONS

Tiangong Wei and Reinhard Klette: "Regularization Method for Depth from Noisy Gradient Vector Fields", Aug. 1, 2002, XP55024121, Auckland, New Zealand.*

(Continued)

*Primary Examiner* — Phuong Huynh
(74) *Attorney, Agent, or Firm* — TraskBritt

(57) ABSTRACT

A nanotopographic measuring device comprises an input arranged to receive sets of measurement data relating to a semiconductor wafer and memory organized into first and second working tables and a results table. A calculation function is capable of establishing a current surface equation from localized gradient values. The equation is established in such a way as to generally minimize a deviation amount between the gradient values calculated from the current surface equation and the localized gradient values. A reconstruction function calculates localized gradient values from a set of measurement data corresponding to an area of the wafer and completes the working tables with these values. It repeatedly calls the calculation function, each time with a part of the values of the first working table and the second working table corresponding to a portion of the area of the wafer to determine, each time, a current surface equation. It completes the results table with the localized height data corresponding to this area, in relation to the reference plane of the wafer, the localized height data being calculated from at least certain of the current surface equations.

17 Claims, 6 Drawing Sheets

(51) Int. Cl.
      *H01L 21/66*       (2006.01)
      *G06F 11/30*       (2006.01)

(56)                References Cited

OTHER PUBLICATIONS

French Search Report for French Application No. 1103073 dated Apr. 12, 2012, 3 pages.
Wei et al., Regularization Method for Depth from Noisy Gradient Vector Fields, Computer Science Department of The University of Aukland, CITR at Tamaki Campus, CITR-TR-115, Aug. 2002, 7 pages.
Wu et al., A Line-Integration Based Method for Depth Recovery from Surface Normals, Computer Vision, Graphics, and Image Processing, vol. 43, (1988), pp. 53-66.
International Written Opinion for International Application No. PCT/FR2012/000395 dated Jun. 12, 2012, 10 pages.
International Preliminary Report on Patentability for International Application No. PCT/FR2012/000395 dated Apr. 8, 2014, 11 pages.
International Search Report for International Application No. PCT/FR2012/000395 dated Jun. 12, 2012, 7 pages.
Chinese First Search for Chinese Application No. 2012800544071, dated Dec. 26, 2015, 1 page.
Chinese Second Office Action for Chinese Application No. 201280054407, dated Sep. 7, 2016, 10 pages.
Chinese First Office Action for Chinese Application No. 201280054407.1, dated Jan. 5, 2014, 17 pages.

* cited by examiner

DEVICE AND METHOD FOR INSPECTING SEMICONDUCTOR MATERIALS

CROSS-REFERENCE TO RELATED APPLICATIONS

This application is a national phase entry under 35 U.S.C. §371 of International Patent Application PCT/FR2012/000395, filed Oct. 4, 2012, designating the United States of America and published as International Patent Publication WO 2013/050673 A1 on Apr. 11, 2013, which claims the benefit under Article 8 of the Patent Cooperation Treaty and under 35 U.S.C. §119(e) to French Patent Application Serial No. 11/03073, filed Oct. 7, 2011, the disclosure of each of which is hereby incorporated herein in its entirety by this reference.

TECHNICAL FIELD

The invention relates to a device and a method for measuring semiconductor products, in particular, in the form of wafers. In the art, the term frequently used for this type of product is "wafer."

BACKGROUND

At the end of their manufacture, semiconductor wafers are systematically inspected, at least in most industrial manufacturing processes. This is done, for example, to search for any defects, which generally occur in the form of heterogeneity of form at the wafer surface.

It is important that this inspection is, in addition to being reliable, fast, or at least that its duration remains compatible with the rest of the production process. In other words, since the inspection is integrated into the manufacturing process of the wafer, the inspection method that is used also affects the rate of production.

Some inspection methods are aimed, in particular, at obtaining measurements relating to the wafer.

On the whole, the measurement methods for semiconductor products are based on optical principles. The spatial wavelength of the measured characteristics form limits to what may be called a field of analysis. Standards applicable to semiconductor products, for example, those known under the name of SEMI standards (from the "Semiconductor Equipment and Materials International" association), define the terminology of the fields of analysis.

Wavelengths of between 15 mm and 300 mm thus reveal defects in the general form of the surface, referred to as flatness defects, whereas wavelengths of between 2 nm and 80 micrometers are used to characterize the surface roughness of the wafer.

The subject here is what is known in the technical field as nanotopography, that is, the assessment of variations in the wafer surface that exhibit wavelengths of between 200 micrometers and 20 nm. Such variations correspond to altitudes relative to a wafer reference plane of between a nanometer and a few tenths of a micrometer. In a way, nanotopography can be viewed as a field of analysis located, in terms of precision, between measurement of the surface finish and measurement of flatness.

What is sought, in particular, is an evaluation for each of multiple areas of the surface, what is known as the "peak-to-valley," that is, the height that separates the highest point in the area under consideration from its lowest point.

In nanotopography, so-called "interferometric" techniques are conventionally used. The light reflected from a reference surface is made to interfere with the light reflected from a surface undergoing inspection. Recent developments involve a so-called "auto-interferometric" method, wherein the reference surface is made up of an area of the surface undergoing inspection, which is next to the area that is undergoing inspection. One then works from one area to the next, each time evaluating a surface area relative to an adjacent area.

On the whole, interferometric techniques give satisfactory results in terms of precision. Their weakness, however, lies in the time required for the acquisition of data and in their sensitivity to movement of the surface, in particular, to vibrations. In practice, the data acquisition operations limit the rate of inspection to around 40 to 60 wafers per hour. Given that today's production systems can manufacture about 100 wafers per hour, it can be seen why a nanotopography inspection station using interferometry cannot be usefully incorporated or joined onto a manufacturing station. Theoretically, it would be necessary to add at least two to three inspection stations to each manufacturing station in order to ensure that inspection operations do not reduce rates of production. Since inspection and manufacture must be carried out in clean rooms, prohibitive costs would result in terms of machine investment and of space that is occupied.

In practice, nanotopography is today only very rarely used systematically for each wafer produced.

The object of this disclosure is to improve that situation.

Disclosure

A device for nanotopographic measurement of semiconductor products, or for helping to measure such products, is proposed, comprising an input interface arranged to receive sets of measurement data relating to a semiconductor wafer, memory organized into a first working table, a second working table and a results table, and a calculation function whose arguments are localized gradient values and is capable of establishing a current surface equation from these localized gradient values. The current surface equation is established in such a way as to generally minimize an amount of deviation between the gradient values calculated from the current surface equation and the localized gradient values. The device includes a reconstruction function arranged to calculate, from a set of data corresponding to an area of the semiconductor wafer, localized gradient values corresponding to a first direction of the semiconductor wafer and to complete the first working table with calculated localized gradient values. The reconstruction function also calculates, from a set of measurement data corresponding to the area of the semiconductor wafer, localized gradient values corresponding to a second direction of the semiconductor wafer and completes the second working table with calculated localized gradient values. The reconstruction function repetitively calls the calculation function with, each time, as arguments, a part of the values of the first working table and of the second working table corresponding to a portion of the area of the wafer, in order to determine, each time, a current surface equation corresponding to the arguments, to complete the results table with the localized height data corresponding to the area of the wafer, which are relative to the reference plane of the wafer. These localized height data are calculated from at least some of the current surface equations.

The proposed device uses measurement data that can be acquired quickly, otherwise than using interferometry, in a few seconds. The production rate will (in practice) only be limited by the manipulation of the wafers. The acquisition rate is close to the rates of production achieved today, including even the most competitive rates of production. For a manufacturing line for substrates with a diameter of 300 mm, these production rates are typically of the order of a hundred or so wafers per hour. One can now envisage adding the proposed device to a manufacturing station for systematic inspection of the wafers produced. The proposed device allows the surface of the semiconductor wafer to be characterized.

The repeatability of the inspection is entirely satisfactory, as has been demonstrated in tests carried out by the applicant.

Also proposed is a method for nanotopographic measurement of semiconductor products, or for helping to measure such products, comprising the steps of receiving sets of measurement data relating to a semiconductor wafer; calculating, from a set of measurement data corresponding to an area of the semiconductor wafer, localized gradient values corresponding to a first direction of the semiconductor wafer; calculating, from a set of measurement data corresponding to the area of the semiconductor wafer, localized gradient values corresponding to a second direction of the semiconductor wafer; repetitively establishing a current surface equation each time from a part of the localized gradient values corresponding to a portion of the area of the wafer, where the current surface equation is established so as to minimize an overall amount of deviation between the gradient values calculated from the current surface equation and the localized gradient values on the portion; and establishing, as measurement data, localized height data corresponding to the area of the wafer, relative to the reference plane of the wafer, where these localized height data are calculated from at least some of the current surface equations.

BRIEF DESCRIPTION OF THE DRAWINGS

Other characteristics and advantages of the invention will appear on examination of the detailed description that follows, and of the accompanying drawings, in which.

The accompanying diagrams are, to a large extent, accurate and true. Consequently, they will serve to provide a better understanding of the detailed description below, and also contribute to the definition of the disclosure where necessary.

DETAILED DESCRIPTION

Figure 1:
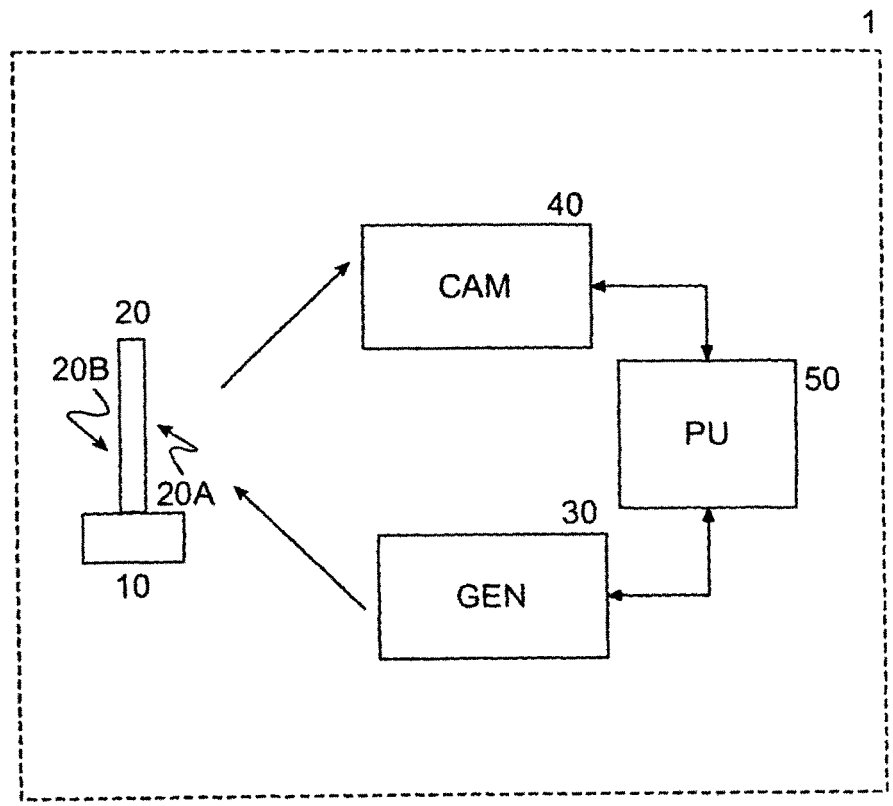
FIG. 1 shows a diagram illustrating a device for inspecting semiconductor products.

FIG. 1 shows a measurement device 1 for semiconductor products. The device 1 comprises a support 10 designed for one or more semiconductor wafers 20 to be measured. In the technical field, the term "wafer" is often used to refer to semiconductor wafer 20. Preferably, wafer 20 is held on the support 10 with no contact on its major faces, namely, a large front face 20A and a large rear face 20B. Preferably, the wafer 20 is held on the support 10 in a vertical position, which prevents any deformation due to the effect of its own weight. For example, the wafer 20 takes the form of a disk. Typically, the diameter of the wafer 20 may be between 100 mm and 400 mm, whereas its thickness is between 200 micrometers and 2 mm.

The device 1 also comprises a pattern generator 30, which generates a light pattern, also called a test pattern, on the large front face 20A of the wafer 20, or at least on one part of this front face 20A. For example, the pattern generator 30 comprises an electronic display device, such as a plasma or liquid crystal display screen linked to a computer's graphic controller, in order to display video signals. The screen may be arranged facing the front face 20A of the wafer 20, parallel to the latter, for example, at a distance of the order of 60 cm.

The device 1 also comprises camera equipment 40 capable of acquiring images of the front face 20A lit by the generator 30. The camera device 40 may comprise a digital camera equipped with a CCD-type ("Charge-Coupled device") or CMOS-type ("Complementary Metal Oxide Semiconductor") sensor. The camera equipment 40 is focused on the front face 20A of the wafer 20, rather than on the mirror image of the screen reflected on this face 20A. For the camera equipment 40, a camera of a type known by the name "DALSA® Pantera 11 M04" may be used, for example.

As an option, a test pattern may also be generated on the rear face 20B and one or more images of this rear face 20B acquired. This may be achieved by providing a second pattern generator and second camera equipment (not shown). The wafer 20 may also be pivoted on itself so as to expose either its rear face 20B or its front face 20A to the test pattern from the pattern generator 30 and to the camera equipment 40.

In addition, device 1 comprises a control unit 50, which is linked both to the pattern generator 30 and to the camera equipment 40. The control unit 50, in addition, receives image data from the camera equipment 40 so that the data can be processed.

Figure 2:
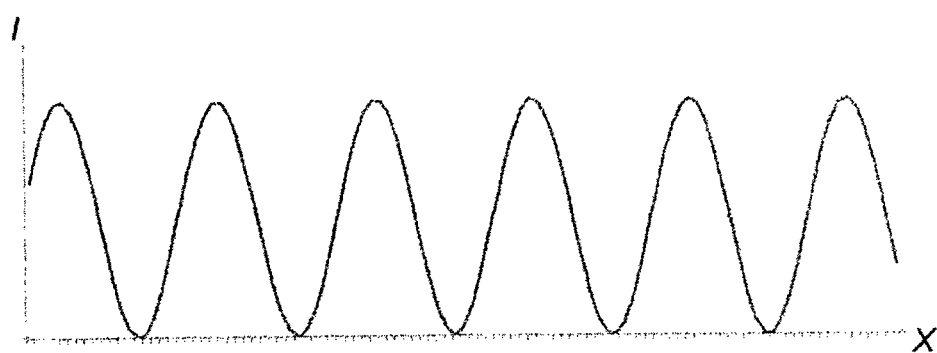
FIG. 2 shows a graph representing the light intensity of a pattern for inspection of semiconductor products.

With reference to FIG. 2, in the plane of the pattern generator, for example, the surface of a screen, the light intensity I varies in a sinusoidal manner in a first direction, here indicated as X, and linearly along a second direction (variation not shown), and perpendicular to the first direction.

The pattern appears as a succession of alternating dark and light bands, where the bands are adjacent to each other along the first direction. The bands are parallel to each other and the direction in which they extend corresponds to the second direction.

Images of test patterns from the pattern generator 30 can be successively acquired, which have spatial frequency or phase characteristics that are potentially different from each other. For example, the bands exhibit a spatial period of 6 mm.

Figure 3:
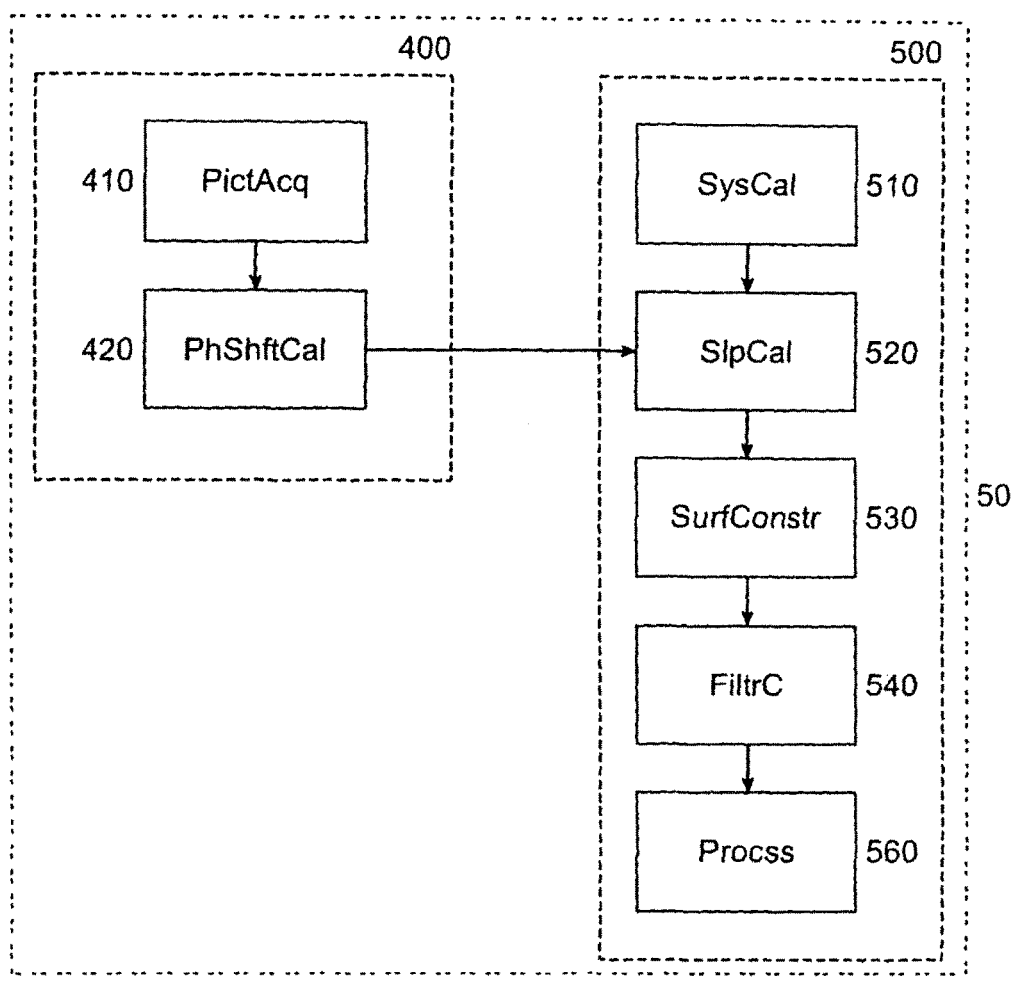
FIG. 3 shows a functional diagram illustrating a part of the control unit for use, for example, in the device of FIG. 1.

With reference to FIG. 3, the control unit 50 comprises an acquisition function 410 that receives image data that come from the light sensor of a camera equipment, for example, camera equipment 40, and records it in a data structure organized into a memory, for example, built into the control unit 50.

Each image is stored in the form of a table of pixels, each of which encodes a grey level value, or any other value that can be related to the light intensity received on the camera equipment light sensor. The rank of the pixel in its line and in its column is indicated respectively and generically as i and j. The pair (i,j) forms the coordinates of the pixel in the image.

In order to carry out measurements on a wafer, the acquisition function 410 stores a first ordered collection of images in memory. The first image of the first collection corresponds to a first relative position of the pattern and the surface to be inspected. In this first position, the direction in which the bands of the projected pattern extend defines a first direction in the plane of the surface of the wafer. This first direction is here designated direction X. Between two successive images of the first collection, the pattern and the wafer have been displaced in relation to each other along a direction indicated as Y, perpendicular to direction X. Preferably, the displacement between two recorded images is made in fixed steps. Advantageously, the pattern generator 30 and the support 10 remain immobile in relation to each other between two recorded images in order to prevent any vibration and to preserve precise mutual positioning of these elements. In this case, it is the projected image that is modified so as to make the pattern move between two image acquisitions of the first collection. For example, the shift between two images may be equal to the ratio of Π over a number of images to be acquired, with this number typically being between 3 and 10 images in each direction.

The acquisition function 410 also stores a second ordered collection of images in memory. The first image of the second collection corresponds to a first position in relation to the pattern and to the surface to be inspected. In this first position, the direction in which the bands extend is perpendicular to the direction X in the plane of the surface. Between two successive images of the second collection, the pattern and the surface of the wafer have been displaced in relation to each other along the direction X, advantageously in a fixed step. In other words, between the images of the first collection and those of the second collection, the pattern has been pivoted by approximately 90° around an axis perpendicular to the wafer 20.

In each location of the image of the front face 20A, the light intensity is, at least approximately, in accordance with the equation in appendix A.1.1. The value $I_0$ represents the mean intensity of the image of the surface of the wafer. The value $A_0$ represents the contrast for the bands of the light pattern. The variable ϕ, which is indicated as PHI below, represents the phase angle. The variable χ represents a spatial coordinate of a first predetermined direction.

The control unit 50 further comprises a phase calculation function 420, which is capable of determining a table of phase values from a collection of images. In this table, each phase value is stored in memory so as to correspond to the coordinates of a pixel of the collection of images. For each pair of coordinates (i,j) there corresponds, in the first collection of images, several grey level values where each grey level value corresponds to the value of the pixel with coordinates (i,j) in an image. It is these multiple values that allow the value of PHI, which corresponds to the coordinates (i,j) to be determined.

For more information of the calculation of this phase, the French patent published as number FR 2 914 422 can be consulted, in particular, pages 12 and 13 of that patent.

Here, the phase calculation function 420 carries out operations on the first collection and on the second collection. A first table of phase values, individually indicated as PHI_X_i,j, is established from the first collection of images, and a second table of phase values, indicated individually as PHI_Y_i,j, is established from the second collection of images. Each i,j represents the coordinates of the value in the table. Each of the first and second tables of phase values may be seen as a phase map.

Figure 4:
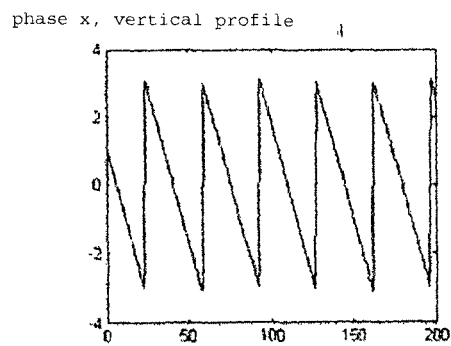
FIG. 4 represents a phase profile along a first direction of the semiconductor product.
Figure 5:
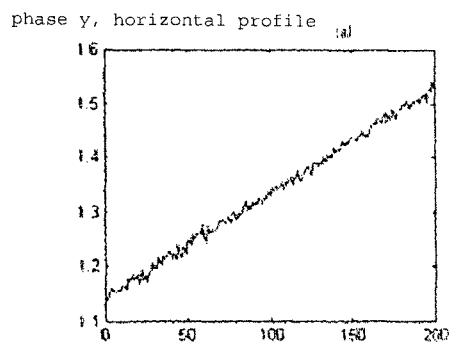
FIG. 5 represents a phase profile along a second direction of a wafer being inspected.
Figure 6:
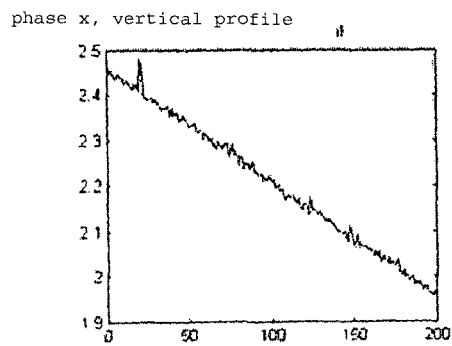
FIGS. 6 and 7 are analogous to FIGS. 4 and 5, respectively, with the wafer being lit under different conditions.
Figure 7:
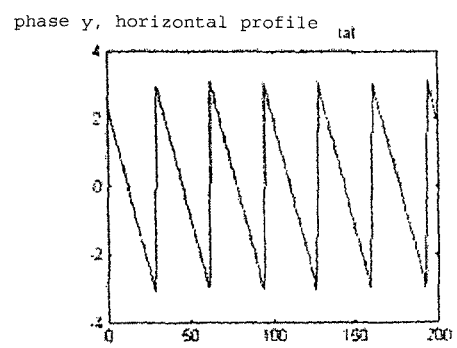

FIGS. 4 to 7 each show a phase map profile relating to a given portion of a wafer. This phase map corresponds to a square of sides having 200 pixels. FIG. 4 shows the variation in the phase PHI_X along a line of the phase map, whereas FIG. 5 shows the variation in this phase over a column. FIG. 6 shows the variation in the phase PHI_Y along a line of the phase map, whereas FIG. 7 shows the variation in this phase over a column.

These curves exhibit a regular general trend: the phase PHI_X in FIG. 5 and phase PHI_Y in FIG. 6 exhibit a general linear trend, phase PHI_X of FIG. 4 and phase PHI_Y of FIG. 7 exhibit general periodic trends, of sawtooth form. In detail, however, these curves exhibit local irregularities.

FIGS. 4 and 7 show that the phase maps are modulated, that is, that their values are in the interval [−Π;Π] and contain phase shifts of 2Π.

The acquisition function 410 and the phase calculation function 420 may be viewed as belonging to a data acquisition module 400. As an option, the control unit 50 comprises, in addition, a module for detection of defects by phase calculation, as is described, for example, in FR 2 914 422, wherein the acquisition function 410 and the phase calculation function 420 are incorporated.

According to the invention, the control unit 50 comprises a nanotopography module 500, capable of interacting with the data acquisition module 400.

The nanotopography module 500 comprises a calibration function 510 that is capable of determining a collection of positioning data relative to certain elements of the device. This data comprises data on the position of the wafer in relation to the pattern generator 30 and to the camera equipment 40. This data can be used to locate in space each point of the wafer 20 to be measured, each pixel of the pattern generator 30 and the exact position of the camera equipment 40. Furthermore, the calibration function 510 may be arranged to collect characteristic data of the optics used for the image acquisition, namely, a transfer function of the lens allowing for aberrations in the latter.

The nanotopography module 500 further comprises a slope calculation function 520, which establishes, from a table of phase values, a table of slope values or slope map. Here the slope calculation function 520 carries out operations on each of the phase maps PHI_X and PHI_Y obtained by the phase calculation function 420. Each slope value is associated with the coordinates (i,j) of the pixel that was used to determine the phase value. This results in a first slope map P_X and a second slope map P_Y.

The nanotopography module 500 comprises a surface reconstruction module 530. From at least one pair of the slope maps, here P_X and P_Y, the surface construction function 530 determines at each pair of coordinates (i,j) a corresponding height value indicated as H_ij. This height is obtained from slope data, in particular P_X_ij and P_Y_ij. The result is a table of values of height relative to a reference plane, which is here called a height map and is indicated as H.

The nanotopography module 500 comprises a filtering function 540, which is applied to the height map H to reveal any defects, that is, portions of the surface that exhibit a height that is substantially greater than the altitude of the rest of the surface reconstructed around this portion.

As an option, a processing function 560 automatically determines defects in the filtered height map.

As an option, the height map H established by the reconstruction function 530 may be subjected to an automatic detection function.

Figure 8:
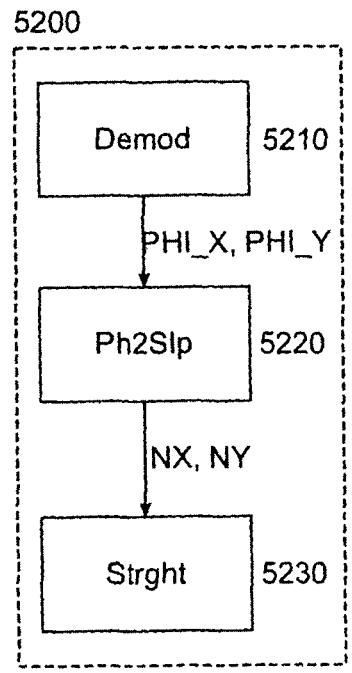
FIG. 8 schematically represents a normal vector's calculation function.

FIG. 8 illustrates an example of a slope calculation function 5200.

The slope calculation function 5200 first comprises a demodulation function 5210, which here carries out operations on each of the phase maps PHI_X and PHI_Y.

The demodulation function 5210 moves along each line of the map PHI_X. Each time that a shift in phase is detected, that is, when the phase value varies suddenly between two adjacent columns, for example, a change from a positive value to a negative value, the value of 2Π (pi) is added to each of the phase values of the next columns in the line being followed.

Analogously, the demodulation function 5210 moves along each column of the map PHI_Y, and adds the value 2Π to the next lines in the column being followed, every time a phase shift is detected.

A conversion function 5220 then receives the demodulated phase maps PHI_X and PHI_Y and calibration data of the type described above.

This data relates to the geometric configuration of the system, in particular, to data on the relative positions of the pattern generator 30, the camera equipment 40 and of the wafer 20, and the spatial position of the locations of the wafer.

The demodulated phase maps PHI_X and PHI_Y are transformed into normal vector maps along the three axial components X, Y, and Z that are indicated respectively as Vx, Vy and Vz, on the basis of a trigonometric calculation.

The maps Vx, Vy and Vz are transformed into a surface gradient comprising two slope maps, indicated as NX and NY. Each gradient value NX_ij corresponds to the ratio Vx_ij over Vz_i,j. Each gradient value NY_ij corresponds to the ratio Vy_ij over Vz_i,j.

A surface smoothing function 5230 then carries out operations on each of the gradient maps NX and NY. For example, the surface smoothing function 5230 comprises a polynomial filter of the order 1 to 4.

Figure 9:
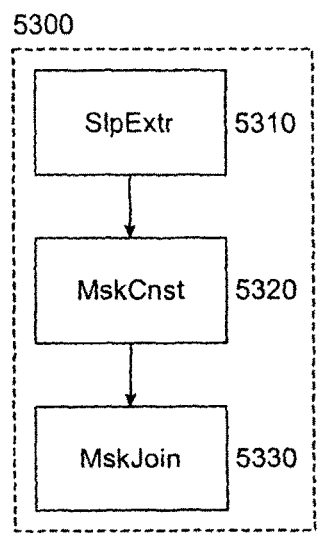
FIG. 9 schematically represents a surface reconstruction function.

FIG. 9 shows an example of a surface reconstruction 5300.

An extrapolation module 5310 receives the slope maps NX and NY after they have undergone surface smoothing.

An extrapolation function 5310 first of all carries out operations on each of the gradient maps NX and NY in order to complete each time the gradient values go beyond the values deduced from the image data.

Figure 10:
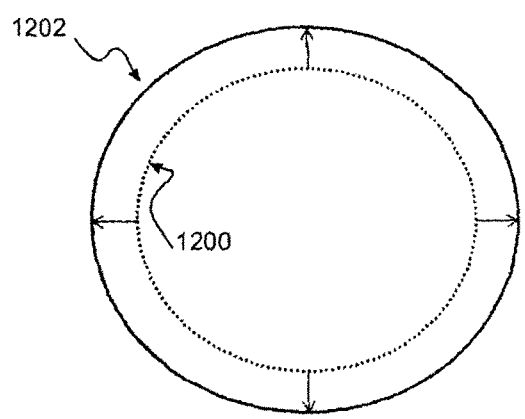
FIG. 10 represents a schematic that illustrates an extrapolation function.

In FIG. 10, for example, the dotted line circle 1200 represents, in the image data, the limit of the wafer. The circle of unbroken line 1202 represents the limit of extrapolation. The gradient tables NX and NY are completed by values extrapolated from limit data. Extrapolation is carried out on the basis of adding values that are calculated by creating a mean over the surroundings of the point to be extrapolated.

The extrapolation function 5310 fills in a binary table, or form, which indicates for each pair of coordinates (i,j) whether it corresponds to a location of the wafer or not. This form was calculated with the generation of the phase tables. Extrapolation is carried out on the data NX and NY. A list of coordinates (i,j) that correspond to the edge of the wafer is established. The coordinates that correspond to the edge of the wafer are on the nearest annular ring of the wafer, that is, which form the non-zero minimum of the distance transform of the binary form. This transform gives, for each pixel (i,j), a minimum distance value separating it from the perimeter, that is, the distance separating the pixel under consideration from the closest null pixel in the Euclidean sense.

To each coordinate in this list is assigned a value calculated from values that correspond to adjacent coordinates in the gradient tables NX and NY. The form distance transform is then updated and a new list of coordinates to be processed is created. The operation is repeated until an extrapolated annular ring of the desired width, for example, close to 5 mm, is obtained.

In a way, the extrapolation function could be considered to have, as an argument, an input table of localized values corresponding to an initial area that it is capable of establishing from the localized values of the input table, extrapolated localized values corresponding to a peripheral area of the initial area. The extrapolation function can be called with at least a part of the gradient maps that correspond to the wafer or to an area of this wafer.

Advantageously, the initial maps NX and NY are retained in the memory.

An elementary reconstruction function 5320 is then called repetitively in order to establish a collection of height maps each time, for what is known as a "thumbnail." A thumbnail is a subset of adjacent coordinates (i,j) that correspond to a restricted area of the wafer. From the sub-set of gradient values corresponding to the thumbnail in the gradient maps NX and NY, the elementary reconstruction function 5320 establishes a surface equation, which associates a height value $z=f(x,y)$ with each coordinate pair (x,y).

The formula in appendix A.1.2. is an expression of a functional W. In this formula, p represents the value of the gradient along X and q, the value of the gradient along Y, each time at the coordinate point (i,j). The function f(x,y) is a surface equation that globally minimizes the functional W over the thumbnail, where the pair (x,y) generically represents the coordinates of a point in the system of coordinates whose axes are parallel to the first and second directions. In other words, for each point (x,y), the function f(x,y) gives a height value that can be indicated as $z=f(x,y)$.

In other words, the elementary reconstruction function 5320 comprises a calculation function having arguments of localized gradient values and that is capable of establishing a current surface equation from these localized gradient values, where the current surface equation is established so as to globally minimize, that is, over the area covered by the localized gradient values received as arguments, an amount of deviation between the gradient values calculated from the current surface equation and the localized gradient values.

This calculation function is called repetitively, with, as arguments, each time part of the values of a first working table and of a second working table comprising localized gradient values in, respectively, two directions of the wafer, and that correspond to the portion of the wafer represented by the thumbnail in order to determine each time a current surface equation corresponds to the arguments.

According to the article by T. Wei and R. Klette, "*Regularization method for depth from noisy gradient vector fields*," CITR Tamaki Campus (CITR-TR-115), Auckland, New Zealand (2002), integration of the formula in appendix A.1.2 can advantageously be carried out in Fourier space by calculating the result of equation A.1.3. In this equation, the function $\hat{f}$ represents the Fourier transform of the function $f$ of appendix A.1.2. The variables u, v, respectively, correspond to the variables x, y in Fourier space. The numbers p* and q* represent the adjoints, or conjugates, of numbers p and q.

Then, for each pair of coordinates (i,j) of the thumbnail to be constructed, the elementary reconstruction function 5320 determines an altitude value Z_ij that it stores in memory while assigning it to the coordinate pair (i,j).

Figure 13:
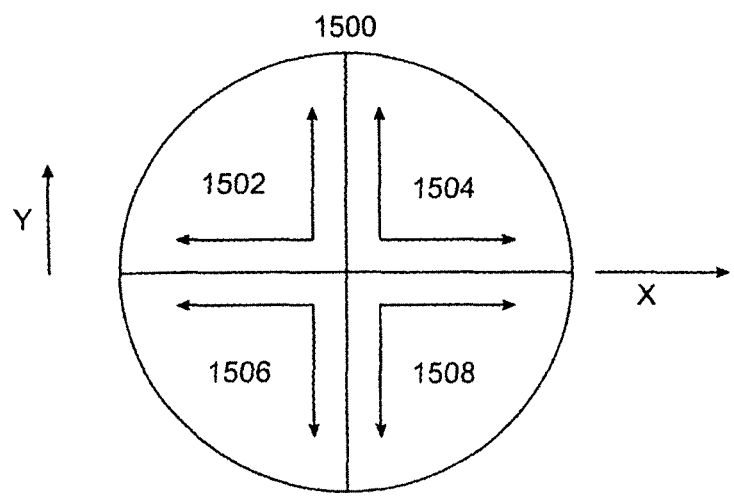
FIG. 13 schematically represents a surface reconstruction function.

For the reconstruction of the wafer surface, an annular ring 1500 of the binary map, extrapolated if necessary, is first divided into four equal quarters in accordance with that shown in FIG. 13. Here, the diameters forming the limits of quarters correspond to the directions X and Y, or are at least parallel to these directions. Each quarter forms an area of the wafer.

A quarter 1502 (top left), quarter 1504 (top right), quarter 1506 (bottom left) and quarter 1508 (bottom right) are processed individually one after the other.

Figure 14:
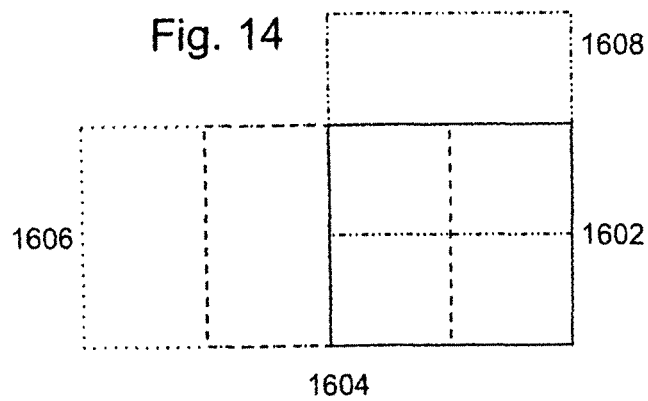
FIG. 14 represents reconstruction and re-patching with overlap of partial elements of the surface.

For example, the quarter 1502 is processed first. A path is shown in FIG. 14.

A thumbnail 1602 is first calculated whose bottom right corner corresponds to the center of the annular ring 1500 of the binary map. The limits of this first thumbnail 1602 are shown as an unbroken line. A corresponding height map is reconstructed, that is, for each coordinate pair (i,j) of this thumbnail, a height value Z_ij is determined from values p_ij and q_ij of maps NX and NY by calling the elementary reconstruction function 5320.

Then, a second thumbnail 1604 is constructed at the first thumbnail 1602, which overlaps the left-hand half of the latter in the figure and which is offset along direction X. The limits of this second thumbnail 1604 are shown in broken lines in FIG. 14. Elementary thumbnails are constructed, superimposed on the previous thumbnail each time, until the edge of the annular ring 1500 is passed. Here, a third thumbnail 1606 shown in a dotted line is reconstructed. A second series of thumbnails is then reconstructed starting from the first thumbnail 1602 and moving along direction Y from the half of the first thumbnail 1602. FIG. 14 gives a fourth thumbnail 1608.

In other words, the elementary reconstruction function 5320 is called successively with arguments formed of parts of gradient maps values that correspond to portions of a quarter of the wafer that partially overlap and that are mutually aligned along the direction X and/or the direction Y.

The reconstructed thumbnails partly overlap each other. In order to obtain an overall reconstructed surface on one quarter, a weighted sum of the thumbnails is made. For each thumbnail, a set of coefficients is applied that favors the center of the thumbnail and gives less importance to the edge.

The table of coefficients applied to each reconstructed thumbnail is a pyramid with a square base. The matrix of coefficients, indicated as C, is given by appendix A.1.6., with the conventions of appendices A.1.7 and A.1.8, where r is the radius of the reconstructed area, or reconstructed thumbnail.

These coefficients are such that their running sum is constant over the entire reconstructed surface. The global altitude map is the sum of each reconstructed thumbnail with the coefficients. This altitude map may be regarded as a results table, which comprises the localized height data corresponding to the entire surface of the wafer, or an area of the latter, relative to the reference plane of the wafer, where this localized height data is calculated from at least some of the current surface equations established by the element reconstruction function.

A surface reconstruction module 5330 is then applied.

Figure 15:
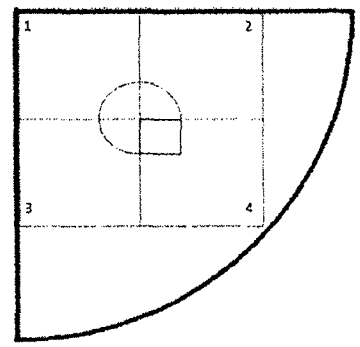
FIG. 15 represents the reconstruction diagram illustrating a global surface reconstruction function.

Each thumbnail has been reconstructed to an integration constant. The reconstruction must be adjusted by minimizing the differences between these integration constants. The integration constant of the first reconstructed thumbnail is arbitrarily set to 0. The integration constants of the following thumbnails are determined using all the information that is already available. Thus, for example, in FIG. 15, which shows the reconstruction of the right lower quarter, the integration constant of thumbnail 4, which was the last to be reconstructed, is calculated so that it connects with each of the neighboring thumbnails, that is, to a side of each of thumbnails 2 (above) and 3 (to the left), the integration constant for thumbnails 2 and 3 having already been calculated.

Figure 11:
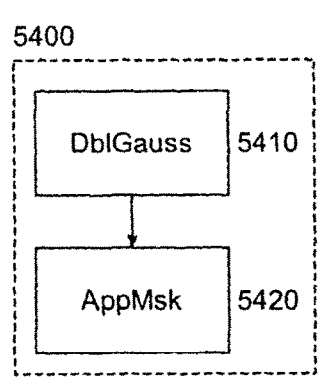
FIG. 11 schematically represents filter function.

Reference is made to FIG. 11, which shows an example of a filter function 5400.

A double Gaussian type high-pass filter 5410 is applied to the altitude map to reduce the low-frequency component. Only the information whose period is between 200 micrometers and 2 cm is retained.

For example, in order to obtain a response G as a function of the wavelength $\lambda$, the SEMI M78 standard indicates a filter that is in accordance with the equation given in appendix A.1.4, where $\lambda c$ designates the cut-off wavelength.

Figure 16:
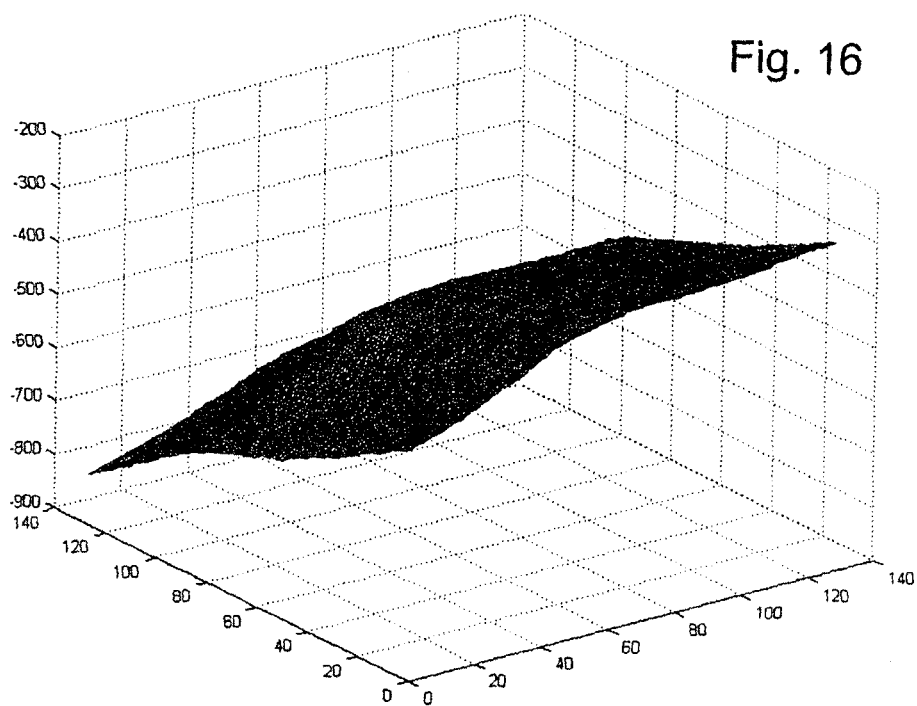
FIG. 16 represents a portion of the reconstructed surface.
Figure 17:
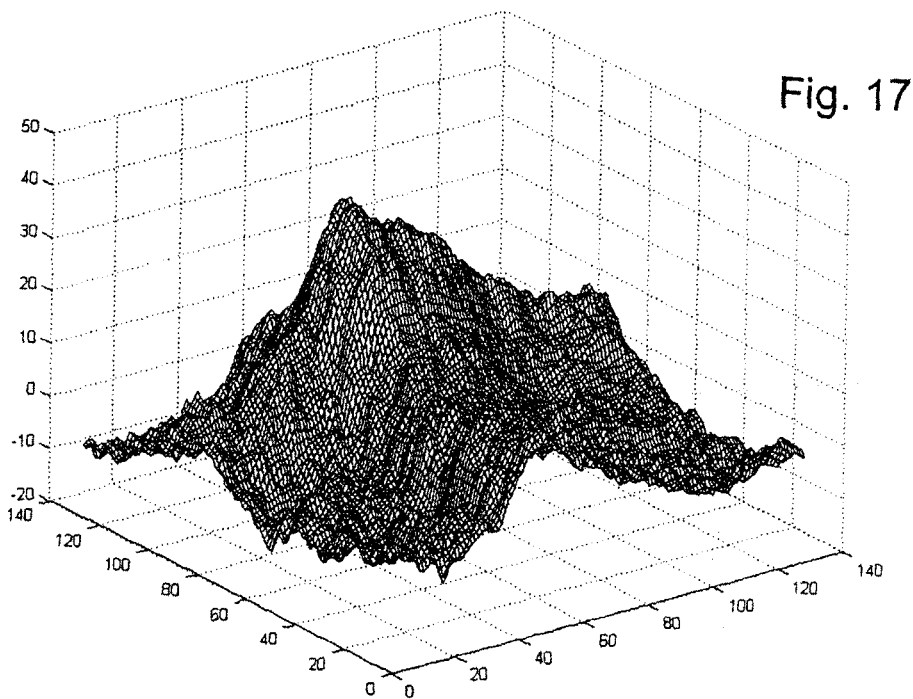
FIG. 17 represents the portion of the surface in FIG. 16 after filtering.

Here, this two-dimensional filter is modified by replacing X, with the formula in appendix A.1.5. The filtered altitudes map is obtained by convolution of the filter in appendix A.1.5 with the global altitude map. FIG. 16 shows a portion of the reconstructed wafer before filtering. Here, one starts to see the general orientation of this portion of the surface, without clearly distinguishing significant irregularities in it. FIG. 17 shows the portion of the wafer of FIG. 16 after filtering. A peak with approximate coordinates (100, 60) can clearly be seen here.

Figure 12:
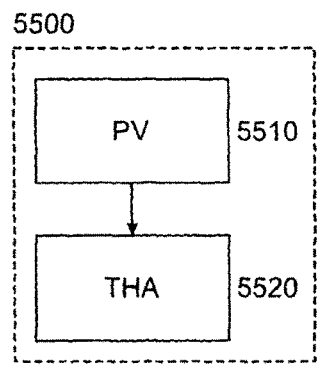
FIG. 12 schematically represents a nanotopography data calculation function.

Reference is made to FIG. 12, which shows an example of an analysis function 5500, or post-processing.

A first analysis sub-function 5510 establishes a Peak-to-Valley (or PV) map. This first analysis sub-function 5510 calculates for each thumbnail the amplitude of the surface reconstructed in a sliding window of predefined shape and size, for example, 2 mm or 10 mm, square or circular. The value thus determined is stored in memory in correspondence with the coordinates of the center of the thumbnail.

A second analysis sub-function 5520 calculates the distribution of PV values, also known as the "Threshold Height Analysis" or THA curve.

The second analysis sub-function 5520 delivers the value of this curve, which corresponds to 0.05%, which corresponds to the altitude of 0.05% of the greatest PV values.

The device that is described offers a certain advantage in that it uses data that are acquired rapidly in comparison with interferometric techniques. The processing of the acquired data can be sped up by multiplying the number of calculation units and/or by carrying out the processes, at least in part, in parallel. Since the acquisition time is short, of the order of around ten seconds, it is possible to measure around a hundred wafers per hour. Consequently it becomes possible to systematically inspect every wafer produced, directly after it is manufactured. The reconstruction method according to the invention allows height maps to be obtained that have very low levels of noise, making them usable in the field of nanotopography.

The control unit 50 has been described in functional terms. In physical terms, this unit comprises, for example, one or more calculation processors, memory, a library of functions corresponding to the modules and functions described, where this library can be stored on the media of the unit, typically a hard disk, or on removable media, for example, of the optical type.

The nanotopography module 500 has been presented as interacting with the data acquisition module 400, at least in that it uses the latter's phase maps. The invention becomes manifest once the functional elements that correspond to the module 500 interact with each other in the manner described, whether they are coupled to a defect detection module or not. More generally, the invention becomes manifest once the wafer surface is reconstructed from height gradient wafers. If necessary, these maps can be fed to a device according to the invention through, for example, an input interface. The nanotopography module can also incorporate the functional elements of the data acquisition module 400 capable of establishing the phase maps in question.

The device that is described includes a camera device in the form, for example, of a digital camera. This device may be suitable for all equipment equipped with a light sensor from which image data can be extracted, or localized light intensity level data.

The invention that has just been described can also be expressed in the form of a method for nanotopographic measurement of semiconductor products that includes the following steps:

receiving sets of measurement data relating to a semiconductor wafer;

calculating, from a set of measurement data corresponding to an area of the semiconductor wafer, localized gradient data that correspond to a first direction of the semiconductor wafer;

calculating, from a set of measurement data corresponding to the area of the semiconductor wafer, localized gradient data that correspond to a second direction of the semiconductor wafer;

repetitively establishing a current surface equation from part of the localized gradient values corresponding to a portion of the area of the wafer, where the current equation is established in such a way as to minimize the overall amount of deviation between the gradient values calculated from the current surface equation and localized gradient values; and establishing, as measurement data, localized height data that corresponds to the area of the wafer, in relation to the reference plane of the wafer, this localized height data being calculated from at least certain of the current surface equations.

This method may include an extrapolation step wherein, from localized gradient data, localized extrapolated values are calculated that correspond to a peripheral area of an initial area, where the extrapolation is carried out on at least a part of the set of data corresponding to the area of the wafer. The localized gradient values that correspond to the first direction of the semiconductor wafer and/or to the second direction of the semiconductor wafer are then calculated from the extrapolated localized data.

The calculation of localized gradient values may comprise a sub-step for calculation of gradient values from measurement data and a sub-step for extrapolation of the gradient values thus calculated to establish the values thus extrapolated as gradient values that are useful for establishing current surface equations.

A correction step may be envisaged wherein smoothed localized gradient values are established prior to the calculation of the current surface equations.

Optionally, current surface equations are successively calculated that correspond to portions of the area of the plate that partially and/or mutually overlap, aligned along the first direction and/or the second direction.

Advantageously, localized height data are calculated that correspond to the area of the wafer, from a weighted sum of the current surface equations. Preferably, the weighting coefficients applied to each thumbnail form a pyramid with a square base.

If necessary, when the current surface equations comprise one or more integration constants, these integration constants are determined in such a way that the successive portions of the semiconductor wafer are joined to each other along their adjacent borders.

The calculation of current surface equations can be carried out by the solution of a functional in Fourier space.

The reconstruction function may be arranged so as to fill in a first intermediate table and a second intermediate table with gradient values calculated from measurement data and then to call the extrapolation function with the first intermediate table and the second intermediate table in order to fill in the first working table and the second working table with extrapolated localized gradient data.

Appendix 1: Mathematical Formulae $$I = I_0(1 + A_0 \cos(\varphi + x))  \quad \text{A.1.1}$$

$$W = \int\int \left(\left(-\frac{\partial f(x,y)}{\partial x}\right) - p\right)^2 + \left(\left(-\frac{\partial f(x,y)}{\partial y}\right) - q\right)^2 dx dy \quad \text{A.1.2}$$

$$\overline{f}(u,v) = \frac{-ju\overline{p}^* - jv\overline{q}^*}{u^2 + v^2} \quad \text{A.1.3}$$

$$G_{DHP} = 1 - 2e^{-1.228\left(\frac{\lambda_c}{\lambda}\right)^2} + e^{-2.456\left(\frac{\lambda_c}{\lambda}\right)^2} \quad \text{A.1.4}$$

$$\lambda = \sqrt{\lambda_x^2 + \lambda_y^2} \quad \text{A.1.5}$$

$$\forall (i,j) \in ([1,r] \times [1,r]), C(i,j) = \frac{1}{2} \times f(i,j) \times f(j,i) \quad \text{A.1.6}$$

$$f(i,j) = \text{sign}(r_2 - i) \times \frac{i-1}{r_2 - 1} \quad \text{A.1.7}$$

$$r_2 = \frac{r}{2} \quad \text{A.1.8}$$

The invention claimed is:

1. A device for nanotopographic measurements of semiconductor products comprising:
   an input interface arranged to receive sets of measurement data relating to a semiconductor wafer;
   memory organized into a first working table, a second working table and a results table;
   a control unit comprising:
      a calculation function whose arguments are localized gradient values, wherein the calculation function is capable of establishing a current surface equation from the localized gradient values, where the current surface equation minimizes a global amount of deviation between calculated localized gradient values calculated from the current surface equation and the localized gradient values;
      a reconstruction function configured to:
         calculate, from a set of measurement data corresponding to an area of the semiconductor wafer, localized gradient values that correspond to a first direction of the semiconductor wafer and to fill the first working table with calculated localized gradient values,
         calculate, from a set of measurement data corresponding to the area of the semiconductor wafer, localized gradient values that correspond to a second direction of the semiconductor wafer and to fill the second working table with calculated localized gradient values,
         repeatedly call the calculation function with, as arguments each time, a part of the values of the first working table and of the second working table corresponding to a portion of the area of the semiconductor wafer, to determine each time a current surface equation corresponding to the arguments,
         fill the results table with localized height data corresponding to the area of the semiconductor wafer, in relation to the reference plane of the semiconductor wafer, where the localized height data is calculated from at least some of the current surface equations.

2. The device of claim 1, wherein the control unit further comprises an extrapolation function whose argument is an input table of localized gradient values that correspond to an initial area and wherein the extrapolation function is capable of establishing, from the localized gradient values in the input table, extrapolated localized gradient values that correspond to a peripheral area of the initial area, wherein the reconstruction function is configured to:
   call the extrapolation function with at least a part of the set of measurement data corresponding to the area of the semiconductor wafer, and
   calculate the localized gradient values corresponding to at least one direction selected from the group consisting of the first direction of the semiconductor wafer and the second direction of the semiconductor wafer from the extrapolated localized data.

3. The device of claim 2, wherein the reconstruction function is configured to fill a first intermediate table and a second intermediate table with localized gradient values calculated from measurement data and then to call the extrapolation function with the first intermediate table and the second intermediate table in order to fill the first working table and the second working table with extrapolated localized gradient data.

4. The device of claim 1, wherein the control unit further comprises a correction function whose argument is an input table of localized gradient values and wherein the correction function is capable of establishing smoothed corresponding localized gradient values, wherein the reconstruction function is configured to call the correction function prior to filling at least one table selected from the group consisting of the first working table and the second working table.

5. The device of claim 4, wherein the correction function is configured to apply a polynomial filter of an order from 1 to 4 to input table values.

6. The device of claim 1, wherein the control unit further comprises a filter function, wherein the reconstruction function is configured to apply the filter function to the results table.

7. The device of claim 6, wherein the filter function comprises a high-pass and double Gaussian filter.

8. The device of claim 1, wherein the reconstruction function is configured to successively call the calculation function with, as arguments, parts of the localized gradient values of the first working table and of the second working table corresponding to portions of the area of the wafer that are partially overlapped.

9. The device of claim 1, wherein the reconstruction function is configured to successively call the calculation function with, as arguments, parts of the localized gradient values of the first working table and of the second working table corresponding to portions of the area of the wafer mutually aligned along a direction selected from the group consisting of the first direction and the second direction.

10. The device of claim 1, wherein the reconstruction function is configured to fill the results table with localized height data that corresponds to the area of the semiconductor wafer calculated from a weighted sum of the current surface equations.

11. The device of claim 10, wherein weighting coefficients applied to each portion of the area of the semiconductor wafer form a pyramid with a square base.

12. The device of claim 11, wherein, at any coordinate point (i,j) of a portion of the area of the semiconductor wafer, the value C(i,j) of the weighting coefficient is given by the following formula:

$$\forall (i,j) \in ([1,r] \times [1,r]), C(i,j) = \frac{1}{2} \times f(i,j) \times f(j,i)$$

wherein $$f(i, j) = \text{sign}(r_2 - i) \times \frac{i-1}{r_2 - 1} \text{ and } r_2 = \frac{r}{2},$$

where r represents the side of the portion.

13. The device of claim 1, wherein the current equations comprise at least one integration constant, and the at least one integration constant is determined so that at least some of the portions of the area of the semiconductor wafer are connected at adjacent edges.

14. The device of claim 1, wherein the calculation function is arranged so as to minimize the deviation by solving a functional in Fourier space.

15. An installation for measuring semiconductor products, comprising:
   a support configured to receive at least one semiconductor wafer;
   at least one light source configured to generate an illumination pattern, where the at least one light source is arranged to selectively orient the illumination pattern along a direction selected from the group consisting of a first direction and a second direction in a principal plane of the at least one semiconductor wafer;

at least one camera device configured to capture at least one image of the illumination pattern; and the device of claim 1.

16. The installation of claim 15, wherein sets of measurement data comprise localized gradient values of phases calculated from the at least one image.

17. A method for nanotopographic measurement of semiconductor products, the method comprising:

receiving sets of measurement data relating to a semiconductor wafer;

calculating, from a set of measurement data corresponding to an area of the semiconductor wafer, localized gradient values that correspond to a first direction of the semiconductor wafer, calculating, from a set of measurement data corresponding to the area of the semiconductor wafer, localized gradient values that correspond to a second direction of the semiconductor wafer, repetitively establishing a current surface equation from a part of the localized gradient values corresponding to a portion of the area of the semiconductor wafer, where the current surface equation minimizes a global amount of deviation between the localized gradient values calculated from the current surface equation and localized gradient values of the portion;

establishing, as measurement data, localized height data corresponding to the area of the semiconductor wafer, relative to a reference plane of the semiconductor wafer, the localized height data being calculated from at least some of the current surface equations.

* * * * *

UNITED STATES PATENT AND TRADEMARK OFFICE
CERTIFICATE OF CORRECTION

PATENT NO. : 9,816,942 B2
APPLICATION NO. : 14/350135
DATED : November 14, 2017
INVENTOR(S) : Philippe Gastaldo and Viviane Leguy Page 1 of 1

It is certified that error appears in the above-identified patent and that said Letters Patent is hereby corrected as shown below:

In the Specification

| | | |
|---|---|---|
| Column 7, | Line 9, | change "indicated as H_ij." to --indicated as H_i,j.-- |
| Column 7, | Line 10, | change "particular P_X_ij and P_Y_ij." to --particular P_X_i,j and P_Y_i,j.-- |
| Column 7, | Line 55, | change "gradient value NX_ij" to --gradient value NX_i,j-- |
| Column 7, | Line 56, | change "Vx_ij over Vz_i,j." to --Vx_i,j over Vz_i,j.-- |
| Column 7, | Line 56, | change "value NY_ij corresponds" to --value NY_i,j corresponds-- |
| Column 7, | Line 57, | change "ratio Vy_ij over" to --ratio Vy_i,j over-- |
| Column 9, | Line 24, | change "altitude value Z_ij" to --altitude value Z_i,j-- |
| Column 9, | Line 44, | change "height value Z_ij" to --height value Z_i,j-- |
| Column 9, | Line 45, | change "p_ij and q_ij of maps" to --p_i,j and q_i,j of maps-- |

Signed and Sealed this
Sixth Day of February, 2018

Joseph Matal
*Performing the Functions and Duties of the
Under Secretary of Commerce for Intellectual Property and
Director of the United States Patent and Trademark Office*